United States Patent [19]

Uenoyama et al.

[11] Patent Number: 5,354,447
[45] Date of Patent: Oct. 11, 1994

[54] BIOSENSOR AND METHOD OF QUANTITATIVE ANALYSIS USING THE SAME

[75] Inventors: Harumi Uenoyama; Hisashi Okuda, both of Kyoto, Japan

[73] Assignee: Kyoto Daiichi Kagaku Co., Ltd., Kyoto, Japan

[21] Appl. No.: 989,590

[22] Filed: Dec. 11, 1992

[30] Foreign Application Priority Data

Dec. 12, 1991 [JP] Japan .................. 3-328657

[51] Int. Cl.⁵ ........................... G01N 27/26
[52] U.S. Cl. .................. 204/403; 204/416; 204/418; 204/409; 435/817
[58] Field of Search ........... 204/403, 418, 416, 409; 435/817

[56] References Cited

U.S. PATENT DOCUMENTS 4,431,507 2/1984 Nankai et al. ............... 204/403
5,120,420 6/1992 Nankai et al. ............... 204/403
5,264,103 11/1993 Yoshioka et al. ............ 204/418

FOREIGN PATENT DOCUMENTS 0359831 3/1990 European Pat. Off. .
0513804 11/1992 European Pat. Off. .
2643150 8/1990 France .

*Primary Examiner*—John Niebling
*Assistant Examiner*—Bruce F. Bell
*Attorney, Agent, or Firm*—Birch, Stewart, Kolasch & Birch

[57] ABSTRACT

A biosensor for electrochemically detecting an electrochemically active material generated by a reaction of a compound to be analyzed in a liquid sample and at least one compound which specifically reacts with the compound to be analyzed, in which a working electrode has at least two electrode parts and the supplied liquid sample contacts the electrode parts successively at an interval, and with which, the electrochemically active material and the compound to be analyzed are quantitatively analyzed separately.

11 Claims, 5 Drawing Sheets

BIOSENSOR AND METHOD OF QUANTITATIVE ANALYSIS USING THE SAME

BACKGROUND OF THE INVENTION

Field of the Invention

The present invention relates to a biosensor and a method of quantitative analysis using the same. More particularly, the present invention relates to a biosensor and a method for detecting and quantitatively analyzing a specific material contained in a liquid sample such as blood, serum, urine, saliva and the like.

Examples of the specific material to be assayed are glucose, lactic acid, cholesterol, alcohol, urea and the like. Examples of compounds which specifically react with these compounds are oxidoreductases. Other electrochemically active compounds include ascorbic acid, uric acid and the like.

While there are various specific materials to be assayed as above, a conventional assay will be explained by making reference to quantitative analysis of lactic acid and ascorbic acid as an example.

Lactic acid reacts with lactate oxidase to produce an electrochemically active material. By measuring an electric current generated in this reaction, a concentration of lactic acid in the liquid sample can be measured. However, the liquid sample often contains other electrochemically active compounds such as ascorbic acid, which interferes an accurate measurement of the concentration of lactic acid.

To solve such problem, the applicants proposed a method of quantitative analysis using a biosensor which comprises a working electrode and a counter electrode and in which a biologically active material such as an enzyme is placed at a part which is remote from an electrode surface so as to separately analyze a desired compound and ascorbic acid (see U.S. patent application Ser. No. 07/883,367 filed on May 15, 1992 and European Patent Application No. 92 108 197.2 filed on May 15, 1992). In this biosensor since the enzyme is placed at a part remote from the electrode, in an early period from the supply of the sample, an electric signal which depends solely on ascorbic acid is detected and thereafter a reaction product of an enzymatic reaction diffuses and reaches the electrode surface whereby a sum of the electric signal depending on ascorbic acid and that depending on the reaction product is detected. Then, the electric signal depending on the reaction product is calculated from the detected signal values.

In the above biosensor, the separation of the electric signals relies on the diffusion of the reaction product. When the blood is analyzed, blood corpuscles greatly influence the diffusion rate so that a hematocrit may have an influence on sensitivity of the assay. When the blood containing a large amount of particles such as erythrocytes is assayed, it is necessary to carry out the assay on the separated serum, while there is no problem when urine or saliva is assayed.

SUMMARY OF THE INVENTION

An object of the present invention is to provide a biosensor which can quantitatively analyze a specific compound in a liquid sample which may contain a particle component such as blood.

Another object of the present invention is to provide a method of quantitative analysis of a specific compound in a liquid sample.

According to a first aspect of the present invention, there is provided a biosensor for electrochemically detecting an electrochemically active material which is generated by a reaction of a compound to be analyzed in a liquid sample and at least one compound which specifically reacts with said compound to be analyzed, wherein a working electrode has at least two electrode parts and the supplied liquid sample contacts said electrode parts successively at an interval.

According to a second aspect of the present invention, there is provided a method of quantitative analysis of a compound to be analyzed in a liquid sample comprising steps of:

supplying the liquid sample on the biosensor of the present invention, detecting an electric signal which depends solely on an electrochemically active material at the first electrode part which the liquid sample contact firstly, after a certain time period from the first contact of the liquid sample with the first electrode part, when the liquid sample reaches the second electrode part, detecting an electric signal which depends on both the electrochemically active material and the compound to be analyzed at the second electrode part, and calculating two electric signals to quantitatively analyze the electrochemically active material and the compound to be analyzed separately.

DETAILED DESCRIPTION OF THE INVENTION

One of the characteristics of the biosensor of the present invention is that the working electrode has at least two electrode parts. An enzyme is placed on at least one of them, while no enzyme is place on the other. The biosensor of the present invention has a groove connecting the plural electrode parts in order that the signal depending on the interfering materials such as ascorbic acid is detected before the liquid sample reaches the electrode part carrying the enzyme. Thereby, the liquid sample firstly contacts the electrode parts carrying no enzyme and then flows through the groove in a certain period of time to reach the second electrode part carrying the enzyme.

Herein, the term "electrochemically active material" is intended to include not only a material which can exchange electrons with the working electrode but also a material which is converted to a material that can exchange electrons with the working electrode by a reaction with a mediator which is placed in the biosensor. Examples of the mediator are potassium ferricyanide, ferrocene, p-benzoquinone and the like.

The biosensor of the present invention will be explained further in detail by making reference to the drawings.

Figure 1:
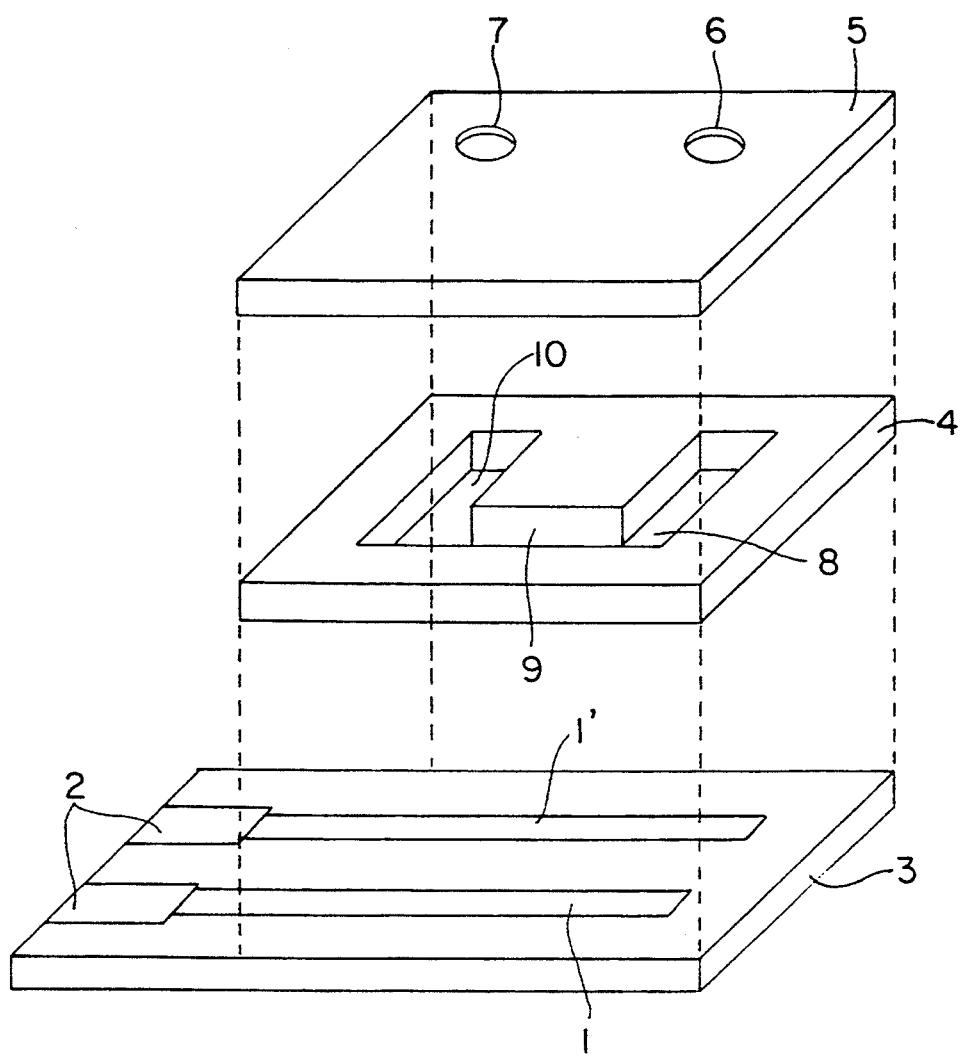
FIG. 1 is an exploded perspective view of a biosensor having two electrode parts according to the present invention.

FIG. 1 is an exploded perspective view of an example of the biosensor according to the present invention.

The biosensor can be produced as follows. The following explanation relates to a biosensor for the quantitative analysis of lactic acid. It is possible to modify the design of the biosensor according to the compound to be analyzed.

On a polyethylene terephthalate sheet substrate 3, carbon electrodes 1, 1' having silver lead wires 2 are formed by, for example, silk screen printing. On the substrate 3, a polyethylene terephthalate spacer 4 having spaces 8, 9, 10 which form a groove for receiving the test liquid sample is adhered with, for example, a double-coated adhesive tape or an adhesive. To fill all the spaces 8, 9, 10, an aqueous solution containing 30 mM of potassium ferricyanide and 1% of hydroxypropylcellulose (30 μl) is dropwise charged and dried to form a solid phase of potassium ferricyanide. Further, on a part of the working electrode 1' in the space 10, an aqueous solution containing 320 mM of potassium ferricyanide, 1% of hydroxypropylcellulose and 20 mg/dl of lactate oxidase (3 μl) was dropwise added and dried to form a solid phase containing the enzyme and potassium ferricyanide. Finally, a polyethylene terephthalate cover plate 5 having an opening 6 for supplying a liquid sample and an opening 7 for removing the sample is adhered to the spacer 4 with, for example, a double-coated adhesive tape or an adhesive to obtain a lactic acid sensor.

EXAMPLES

Using the biosensor produced as above, lactic acid in blood was quantitatively analyzed. Concentrations of lactic acid and ascorbic acid were changed as indicated in FIGS. 2 and 3.

A blood sample was absorbed from the opening 6 and a first voltage of +200 mV was immediately applied between the electrodes 1 and 1'. After 5 seconds, an electric current was measured. The first measured electric current shown in FIG. 2.

The blood sample, which filled the space 8 only during the measurement of the first electric current, flowed through the space 9 and reached the space 10. At this time, the enzyme firstly reacted with lactic acid in the blood sample. After 115 seconds from the charge of the blood sample in the space 8, the second voltage of +200 mV was applied for 5 seconds. Thereafter the second electric current was measured. The measured second electric current is shown in FIG. 3.

Figure 2:
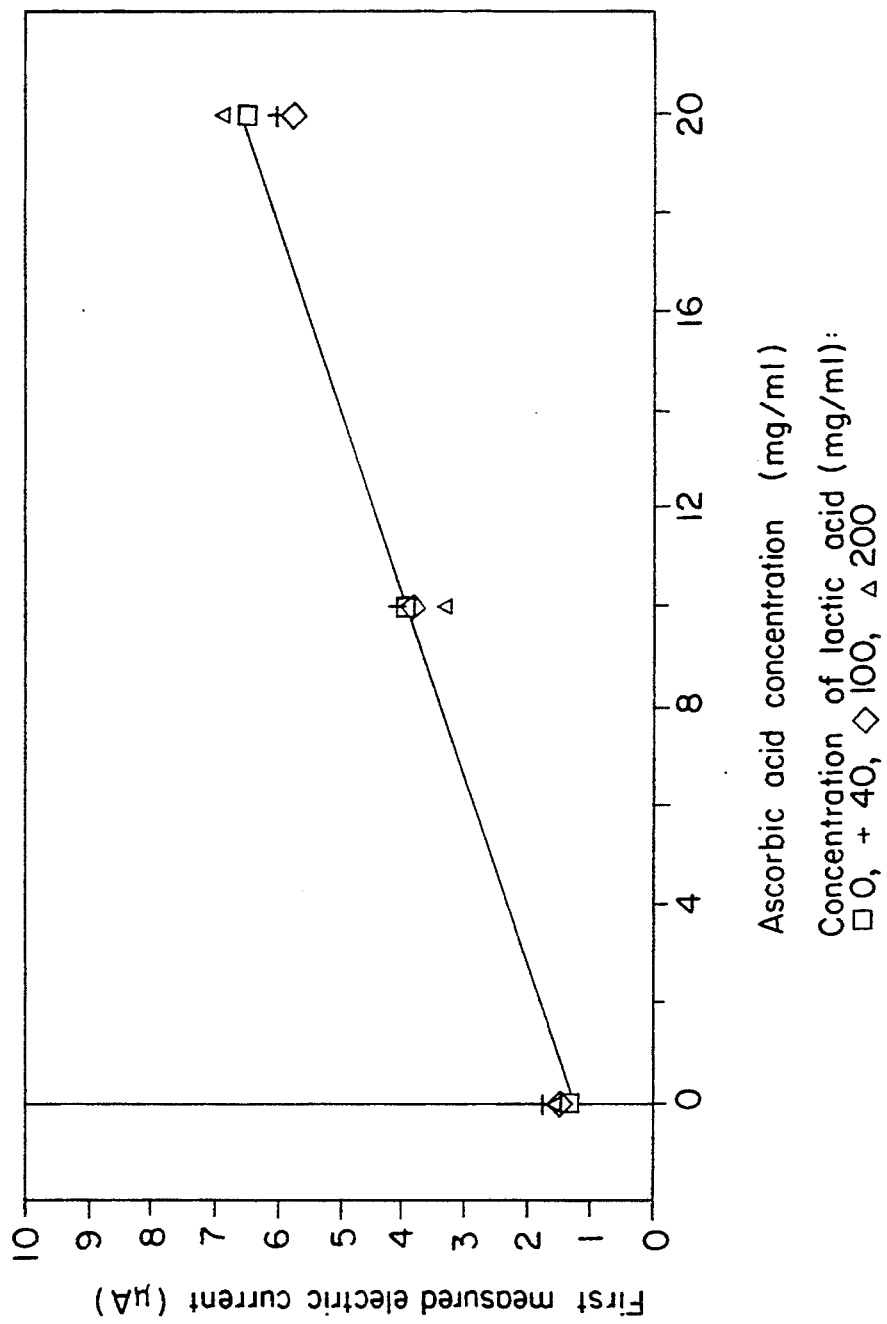
FIG. 2 is a calibration curve of the firstly measured electric current against ascorbic acid.
Figure 3:
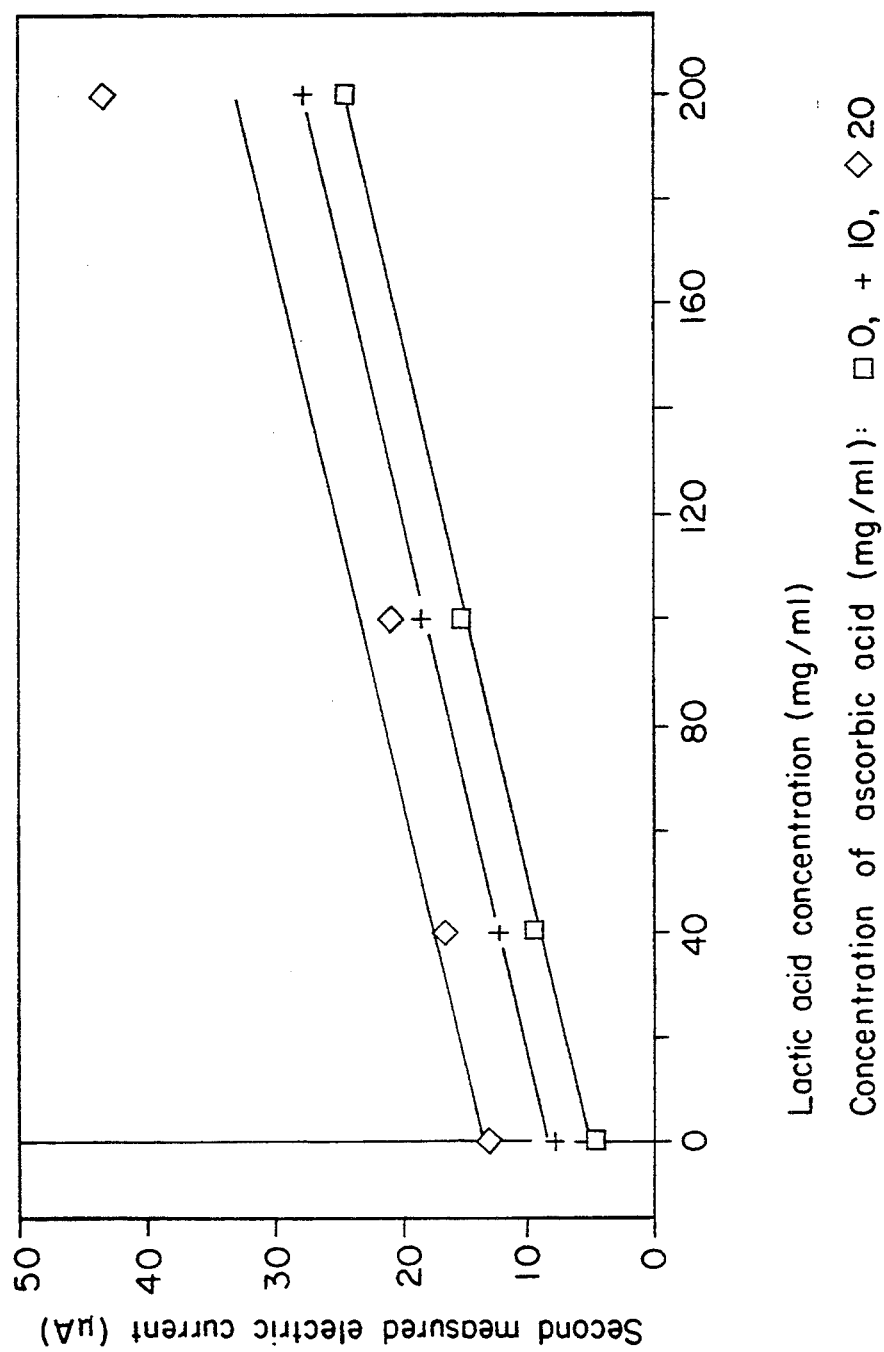
FIG. 3 is a calibration of the secondly measured electric current against lactic acid.

FIG. 2 shows a calibration curve of the first measured electric current depending on the concentration of lactic acid against the concentration of ascorbic acid. In spite of wide variation of the concentration of lactic acid from 0 to 200 mg/dl, the electric currents fell substantially on one line. This means that the concentration of ascorbic acid is measured without the influence of lactic acid.

FIG. 3 shows a calibration curve of the second measured electric current depending on the concentration of ascorbic acid against the concentration of lactic acid. As the concentration of ascorbic acid increased, the line shifted upwardly depending on the response current corresponding to the concentration of ascorbic acid. This means that ascorbic acid has a positive interference on the measurement of the concentration of lactic acid.

Figure 4:
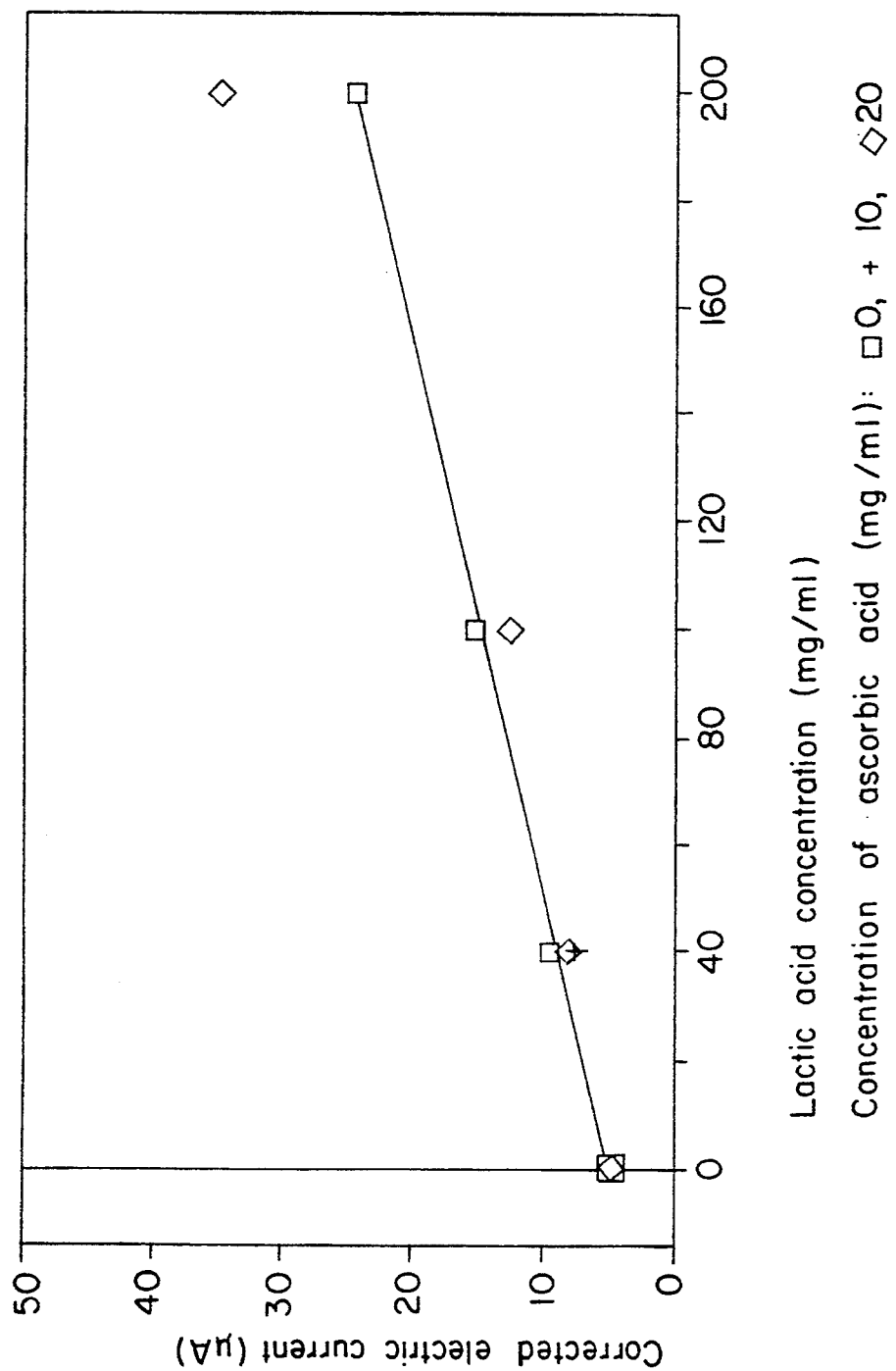
FIG. 4 is a calibration curve which is obtained by correcting the calibration curve of FIG. 3 with the calibration curve of FIG. 2.

Then, the calibration curve of FIG. 3 was corrected using the calibration curve of FIG. 2. The corrected calibration curve is shown in FIG. 4. In spite of wide variation of the concentration of ascorbic acid, the corrected electric currents fell on one line. This means that the concentration of lactic acid was measured with suffering no influence of ascorbic acid.

Figure 5:
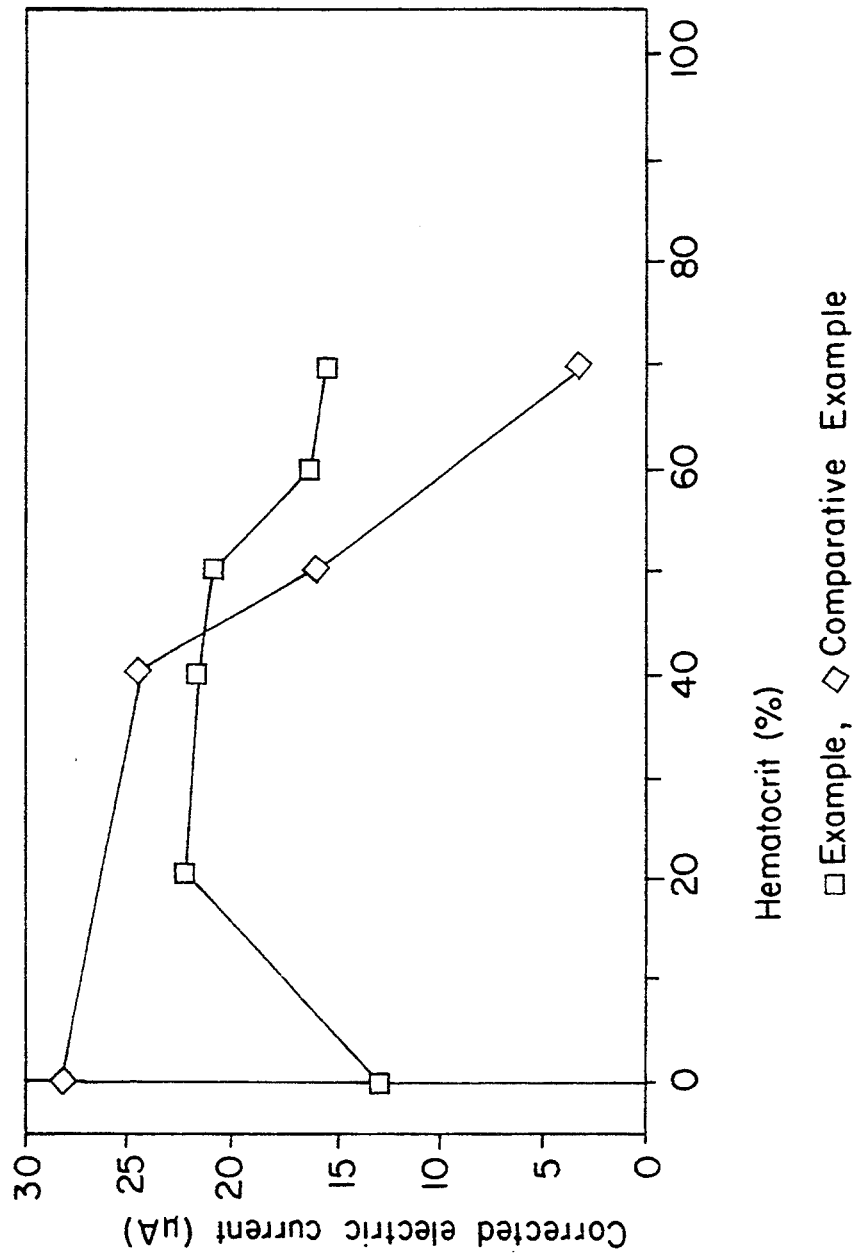
FIG. 5 is a graph showing the influence of hematocrit on the analysis of lactic acid in the method of the present invention and the conventional method.

To a blood sample which was prepared by mixing serum and blood corpuscles in a specific ratio, lactic acid was added in a concentration of 100 mg/dl, and the electric currents were measured using the same biosensor as used in the above analysis. The corrected electric currents are shown in FIG. 5.

For comparison, using the biosensor for the analysis of lactic acid disclosed in U.S. patent application Ser. No. 07/883,367 filed on May 15, 1992 and European Patent Application No. 92 108 197.2 filed on May 15, 1992, the same blood sample as above was analyzed. The corrected electric currents are shown in FIG. 5.

In the comparative test, as the hematocrit increased, the sensitivity decreased, in particular, at a hematocrit of 40% or larger. With the biosensor of the present invention, the sensitivity was not decreased up to 50% of hematocrit. Therefore, the biosensor of the present invention can quantitatively analyze lactic acid in whole blood without the influence of hematocrit.

What is claimed is:

1. A biosensor for electrochemically detecting an electrochemically active material which is generated by a reaction of a compound in a liquid sample to be analyzed and at least a first compound which specifically reacts with said compound to be analyzed, wherein a working electrode has at least two electrode parts and the liquid sample contacts said electrode parts successively in time.

2. The biosensor according to claim 1, wherein said first compound is placed on only one of said electrode parts.

3. The biosensor according to claim 1, wherein a mediator is placed on at least one of said electrode parts.

4. A method of quantitative analysis of a compound to be analyzed in a liquid sample comprising steps of:
   supplying the liquid sample on a biosensor claimed in claim 1,
   detecting an electric signal which depends solely on an electrochemically active material at the first electrode part which the liquid sample contact firstly,
   after a certain time period from the first contact of the liquid sample with the first electrode part, when the liquid sample reaches the second electrode part, detecting an electric signal which depends on both the electrochemically active material and the compound to be analyzed at the second electrode part, and
   calculating two electric signals to quantitatively analyze the electrochemically active material and the compound to be analyzed separately.

5. A sensor for the electrochemical measurement of an analyte and an interfering material contained in a sample consisting essentially of:
   a single pair of electrodes, said pair having a counter electrode and a measuring electrode, wherein said measuring electrode comprises two portions, a first portion of which reacts electrochemically with said interfering material, and a second portion of which comprises a biologically active material which specifically reacts with an analyte to produce an intermediate which is also electrochemically active with the measuring electrode, wherein said first and second portions of the measuring electrode are joined by a channel which conducts the sample from said first portion to said second portion.

6. The biosensor according to claim 5, wherein said biologically active material is an enzyme, which generates an electrochemically active species.

7. The biosensor according to claim 5, wherein said analyte is a substance selected from the group consisting of glucose and lactic acid.

8. The biosensor according to claim 5, wherein said sample is a sample selected from the group of blood, urine and saliva.

9. The biosensor according to claim 5, wherein said measuring electrode carries a mediator.

10. The biosensor according to claim 9, wherein said mediator is a ferricyanide.

11. The biosensor according to claim 10, wherein said ferricyanide is potassium ferricyanide.

* * * * *